(12) United States Patent
Dicianna

(10) Patent No.: US 7,198,780 B2
(45) Date of Patent: Apr. 3, 2007

(54) SELF-TANNING COMPOSITION IN SHEETED SUBSTRATE

(76) Inventor: Valerie Dumont Dicianna, 90 Moyal Court, Concord (CA) L4K 4R8

( * ) Notice: Subject to any disclaimer, the term of this patent is extended or adjusted under 35 U.S.C. 154(b) by 450 days.

(21) Appl. No.: 10/647,313

(22) Filed: Aug. 26, 2003

(65) Prior Publication Data

US 2004/0126342 A1    Jul. 1, 2004

Related U.S. Application Data

(63) Continuation-in-part of application No. PCT/CA02/00234, filed on Feb. 26, 2002.

(51) Int. Cl.
| *A61K 8/00* | (2006.01) |
| *A61K 8/04* | (2006.01) |
| *A61K 36/00* | (2006.01) |
| *A61Q 17/00* | (2006.01) |
| *A61Q 17/04* | (2006.01) |
| *A61Q 19/00* | (2006.01) |

(52) U.S. Cl. .................. 424/59; 424/60; 424/400; 424/401; 424/725

(58) Field of Classification Search ............ 424/59, 424/60, 400, 401
See application file for complete search history.

(56) References Cited

U.S. PATENT DOCUMENTS

| 5,017,365 A |   | 5/1991  | Niedbala |         |
|-------------|---|---------|----------|---------|
| 5,306,486 A |   | 4/1994  | McCook et al. |    |
| 5,514,367 A | * | 5/1996  | Lentini et al. | 424/59 |
| 5,552,135 A |   | 9/1996  | Cioca et al. |      |
| 5,705,145 A |   | 1/1998  | Miklean et al. |    |
| 5,972,360 A |   | 10/1999 | Braun    |         |
| 6,153,208 A | * | 11/2000 | McAtee et al. | 424/402 |
| 6,630,163 B1 | * | 10/2003 | Murad | 424/464 |
| 2002/0071859 A1 |   | 6/2002  | Gott et al. |     |
| 2003/0012809 A1 |   | 1/2003  | Gott et al. |     |

FOREIGN PATENT DOCUMENTS

| JP | 55097939 | 2/1982 |
| WO | WO 94/18933 | 9/1994 |
| WO | WO 99/50379 | 10/1999 |
| WO | WO 99/66897 | 12/1999 |
| WO | WO 02/34224 A1 | 5/2002 |
| WO | WO 02/064107 A1 | 8/2002 |

\* cited by examiner

*Primary Examiner*—Shelley A. Dodson
(74) *Attorney, Agent, or Firm*—Marks & Clerk; Richard Mitchell; Hetal Kushwaha

(57) ABSTRACT

A plurality of sheet-like substrates infused by an aqueous self-tanning position is enclosed in a dispensing enclosure, from which they may be removed one at a time. The self-tanning composition adheres to each substrate while in the container, and transfers from the substrate when applied to the skin of a user. The aqueous self-tanning composition comprises 45% to 65% by weight of aqueous extract of Japanese green tea, 5% to 15% dihydroxyacetone, 5% to 25% ethylethoxydyglycol, 3% to 10% PPG-12-Buteth-16, 1% to 13% of a humectant, 0.05% to 0.5% of minerals, and other trace constituents such as an exfoliator, moisturizer, colorant, anti-oxidant, tanning accelerator, preservative, and sunscreen. The substrates are infused by being placed in a vacuum chamber in which they can be agitated and tumbled, and the ingredients are added in a specific order at specific temperatures, with tumbling and agitation following each step for a specific period of time.

17 Claims, 1 Drawing Sheet

SELF-TANNING COMPOSITION IN SHEETED SUBSTRATE

This application is a Continuation-in-Part of PCT/CA02/00234 filed 26 Feb., 2002

FIELD OF THE INVENTION

This invention relates to sheet-like substrates such as towelettes, wipes, or the like, which are infused with a self-tanning composition, and which are supplied in suitable containers such as canisters, where the container includes a plurality of similar sheet-like infused substrates. In particular, the present invention relates to the provision of a plurality of self-tanning wipes which are supplied in a suitable sealed container to be removed therefrom by being dispensed one at a time. The present invention also relates to the formulation for a self-tanning composition, and to the method of infusing the self-tanning composition into sheet-like substrates.

BACKGROUND OF THE INVENTION

Many people desire to have a "tanned" look, even in the middle of winter. Indeed, many people are advised by their doctors not to expose themselves to significant amounts of sunlight, but want to look tanned.

The tanned look comes generally as a consequence of an excess of melatonin—skin coloring pigment—rising to be near the surface of the skin. In summer time, and in sunny areas, exposure to sunlight, and especially to ultraviolet rays of sunlight, will result in tanning.

Other people will attend tanning salons, where they will expose themselves to excessive amounts of ultraviolet radiation while lying on a so-called "tanning bed", in order to become tanned.

On the other hand, many persons wishing to obtain a tanned appearance will employ a tanning composition, of which many examples are found in the commercial market. Almost universally, those compositions rely on the presence of dihydroxyacetone, which promotes the migration of melatonin to the skin surface. Unfortunately, many commercially available products have a tendency to leave an orange or yellow color, which is quite unsightly.

Also, most commercially available self-tanning compositions are available as a liquid—usually, a low viscosity liquid—or in a cream or a salve. The use of such materials, however, may result in an uneven application of the active ingredient of the self-tanning composition—dihydroxyacetone—to the skin, and as a consequence there may be a streaked or blotchy appearance.

Moreover, many self-tanning compositions which are currently available in the market have an unpleasant odour.

One product is now available in the market, as noted hereafter, in the form of a towelette which is enclosed in an hermetically sealed package. However, that product tends to be wet; and depending on the amount of skin to be treated, there may be a necessity to open and employ several towelettes from several sealed packages. Still further, the self-tanning composition is saturated in a towelette which has a substantial amount of wood pulp fibre in its composition, for exfoliation purposes. The use of such exfoliating towelettes results in microlaceration of the skin, which effectively is traumatic to the skin because it may cause irritation, cuts and nerve exposure. Also, because of the presence of the wood pulp fibre, the wiping action tends to be uneven, causing uneven deposit of the active ingredients of the self-tanning composition, and thereby once again resulting in streaked and/or blotchy appearance.

The present invention, on the other hand, provides a medium for transporting and transferring a self-tanning composition to the skin, where the medium is infused with the self-tanning composition, and is such that the self-tanning composition will transfer evenly to the skin of the user. To that end, the present invention provides a sheet-like substrate which is infused with a self-tanning composition. That composition is aqueous, and the material of the sheet-like substrate provides a transport medium for carrying the various ingredients of the self-tanning composition whether or not they are soluble in the aqueous medium which is the principal component of the self-tanning composition. Another aspect of the present invention provides a method for manufacturing the sheeted self-tanning composition application dispensing set which comprises a plurality of sheet-like substrates that are infused with the self-tanning composition, and where a plurality of similar sheet-like substrates which are infused with the self-tanning composition are packaged together in a dispensing enclosure. The method provides a series of steps whereby a more even and more complete distribution of the various ingredients of the self-tanning composition is achieved throughout the physical matrix of the sheet-like substrates, as discussed hereafter.

In one aspect of the present invention, an exfoliant is provided in the composition, in which the exfoliant effects an enzymatic reaction to the surface of the skin so as to form a residue which can be easily washed away by the aqueous composition as it is being applied to the skin.

Of course, as is usual with any self-tanning composition, it is recommended that it be applied only to thoroughly scrubbed skin following a bath or shower, so that no rough patches or excessive dead skin areas exist which may cause an uneven tan.

DESCRIPTION OF THE PRIOR ART

Braun U.S. Pat. No. 5,972,360 issued Oct. 26, 1999 teaches a self-tanning product which includes a towelette that is impregnated with a self-tanning composition. The product is said to be non-streaking; but since the towelette component preferably contains wood pulp fibres to provide an exfoliation effect during application of the tanning solution, practical experience suggests that streaking or blotching may occur. The ingredients of the self-tanning composition include de-ionized water in a range of 60% to 75% by weight, dihydroxyacetone in a range of 2.5% to 7% by weight, ethoxydiglycol in a range of 10% to 20% by weight, together with fragrances, humectants, stabilizers for the fragrances, preservatives, and a pH adjuster. A towelette is folded and placed into a pouch, which is then filled with the liquid self-tanning composition, after which the pouch is sealed.

WIPO publication 00/13655, published 16 Mar. 2000, is the publication of the PCT cognate of the above noted Braun United States patent.

U.S. Pat. No. 4,343,403 issued Aug. 10, 1982 to Daniels et al teaches towelettes which are impregnated with polyvinyl acetate latex, and which are intended for use in pre-moistened condition as skin cleansing tissues. The packaged sheets are sold in closed containers or in individual sealed water impervious envelopes; and in any event are maintained in contact with the dilute aqueous solution of a precipitating or gelling agent for polyvinyl alcohol, such as boric acid.

A similar system for water disbursable towelettes which are impregnated with non-aqueous lotion formulations is taught in Koltisko U.S. Pat. No. 5,256,417 issued Oct. 26, 1993. Here, the pre-moistened towelettes are intended for use in the medical, cosmetic, or personal care industries with appropriate formulations impregnated therein. The towelettes carry a polyvinyl alcohol binder, or an aqueous polymer emulsion containing polyvinyl alcohol as the protective colloid, and are maintained in a wet condition within the package by contact with a non-aqueous lotion composition which is a liquid organic compound that is insoluble in polyvinyl alcohol.

WIPO publication 00/56271, published 28 Sep. 2000 in the name of Znaiden et al teaches a disposable towelette having a flexible substrate such as cellulosic tissue which is impregnated with α-hydroxycarboxylic acid delivered in a cosmetically acceptable carrier. The purpose of the impregnated towelette is to provide a method for cleansing the skin and simultaneously inhibiting fine lines and wrinkles on the skin.

WIPO publication 00/56277, also published 28 Sep. 2000 in the name of Slavtcheff et al, teaches a cosmetic towelette having a flexible substrate of cellulosic tissue which, in this case, is impregnated with an astringent salt of a metal. The publication teaches a method for removing sebum and reducing perceived oil and greasiness on the skin by wiping the skin with a towelette impregnated with the astringent salt of a metal.

Ziegler et al in U.S. Pat. No. 5,232,688 issued Aug. 8, 1993 teaches a self-tanner cosmetic composition which includes an α-hydroxy substituted ketone or aldehyde, such as dihydroxyacetone, together with a polyacrylamide and a pharmaceutically acceptable carrier. Typically, there is also incorporated at least 15% of polypropylene glycol to improve color intensity.

A similar composition is taught in a related U.S. Pat. No. 5,302,378 issued Apr. 12, 1994 to Crotty et al. Here, an anionic silicone copolyol such as dimethicone copolyolphosphate is also employed.

Tanner et al U.S. Pat. No. 5,514,437 issued May 7, 1996 teaches an artificial tanning composition with improved stability, also employing the use of dihydroxyacetone together with a salt which may be a metabisulfite salt, a sulfite salt, a hydrogen sulfite salt or mixtures thereof.

Takata et al U.S. Pat. No. 5,620,681 issued Apr. 15, 1997 teaches a self-tanning cosmetic composition which contains dihydroxyacetone together with polyoxyethylene-polyoxypropylene block polymer surfactant. The composition contains less than 10% oil; and includes water, alcohol, a water-soluble cellulose type thickening agent and/or xanthane gum and a chelating agent.

U.S. Pat. No. 5,662,890 issued Sep. 2, 1997 to Punto et al teaches a sprayable cosmetic composition which is applied to the skin in an atomized droplet form. The composition includes from 2.5% to 10% by weight of dihydroxyacetone, and from 5% to 75% by weight of one or more penetration enhancers, in an aqueous base which is free of oil or alcohol.

Hansenne U.S. Pat. No. 5,679,656 issued Oct. 21, 1997 teaches an artificial tanning composition which is applied topically, and which comprises dihydroxyacetone together with at least one alkylpolysaccharide and at least one fatty alcohol. There may also be at least one polysaccharide.

Yet another artificial tanning composition is taught in Ascione et al U.S. Pat. No. 5,858,334 issued Jan. 12, 1999. Here, an ultrafine oil-in-water emulsion is taught which is devoid of lipid vesicles, and which contains dihydroxyacetone. The average particle size of the globules which comprise the oily phase of the emulsion characteristically range from 100 nm to 1000 nm.

Another United States patent issued to Crotty et al is U.S. Pat. No. 5,972,314 issued Oct. 26, 1999. That patent teaches a self-tanner cosmetic composition which includes a crosslinked non-emulsifying siloxane elastomer and a volatile siloxane.

Menzel et al U.S. Pat. No. 6,007,796 issued Dec. 28, 1999 teaches a cosmetic self-tanning agent which has a sunscreen effect. Here, as well as dihydroxyacetone, the self-tanning agent contains UV filters, an antioxidant, a moisturizer, and cosmetic carrier substances and additives.

Castro et al U.S. Pat. No. 6,113,888 issued Sep. 5, 2000 teaches a self-tanning mousse where a nitrogen-free polymer and a nitrogen-free surfactant are employed. This provides a single water phase composition, which may also include a nitrogen-free foam booster.

SUMMARY OF THE INVENTION

In accordance with one aspect of the present invention, there is provided a sheeted self-tanning composition application dispensing set which comprises a plurality of sheet-like substrates and a dispensing enclosure. Each of the sheet-like substrates is infused with an aqueous self-tanning composition.

The plurality of sheet-like substrates is arranged in the dispensing enclosure for dispensing therefrom, one sheet at a time.

Each sheet-like substrate is such that the aqueous self-tanning composition adheres to the sheet-like substrate when it is within the dispensing enclosure, and it is also such that the aqueous self-tanning composition will transfer form the sheet-like substrate when it is applied to the skin of a user.

The aqueous self-tanning composition comprises from 45% to 65% by weight of aqueous extract of Japanese green tea, from 5% to 15% by weight of dihydroxyacetone, from 5% to 25% by weight of ethoxydiglycol, from 3% to 10% by weight of PPG-12-Buteth-16 as an emollient, from 1% to 13% by weight of a humectant, and from 0.05% to 0.5% by weight of cosmetically acceptable and compatible minerals.

The self-tanning composition may further comprise cosmetically acceptable and compatible additives, chosen from the group consisting of from 0.5% to 5% by weight of bacillus ferment as an enzyme exfoliator, from 0.5% to 5% by weight of frankincense extract as a moisturizer, from 0.1% to 7.5% by weight of a skin protectant, from 0.1% to 6% by weight of a cosmetically acceptable and compatible colorant, from 0.5% to 1.5% by weight of tocopherol as an anti-oxidant, from 0.1% to 1% by weight of disodium ethylenediamine tetraacidic acid (EDTA), from 1% to 5% by weight of a tanning accelerator, from 0.5% to 1% by weight of a cosmetically acceptable and compatible preservative, from 0.5% to 1% by weight of PPG-40-castor oil as a stabilizer, from 0.1% to 0.5% by weight of natural essential oils, and mixtures thereof.

The humectant which is employed may be 1% to 5% by weight of butylene glycol, 1% to 8% by weight of glycerine, and mixtures thereof.

The skin protectant may be 0.5% to 2.5% by weight of aloe vera gel, from 0.5% to 4% by weight of hydrocotyl extract, from 0.1% to 1% by weight of myrrh extract, and mixtures thereof.

The cosmetically acceptable and compatible colorant, apart from the minerals which also function as a colorant, may be 1% to 5% by weight of walnut extract, 0.1% to 1% by weight of caramel, and mixtures thereof, together with the minerals.

As to the minerals, they may be chosen from the group consisting of C.I. #15985, #77492, #77491, #77499, #77718, #42090, #16035, and mixtures thereof.

A tanning accelerator may be employed, which is chosen from the group consisting of acetyl-L-tyrosine, hydrolyzed vegetable protein, adenosine triphosphate, riboflavin, and mixtures thereof.

The cosmetically acceptable and compatible preservative may be chosen from the group consisting of methyl paraben, dimethylol dimethyl hydantoin, and iodopropynyl butylcarbamate, and mixtures thereof.

Still further, the self-tanning composition may further comprise from 0.5% to 20% by weight of sunscreen chosen from the group consisting of from 1% to 20% by weight of octyl methoxycinnamate, from 1% to 20% by weight of octyl salicylate, from 1% to 10% by weight of benzophenone-3, from 0.5% to 10% by weight of benzophenone-4, and mixtures thereof.

As to the material of the sheet-like substrates employed in the sheeted self-tanning composition application dispensing sets in keeping with the present invention, that material may be woven fabrics, non-woven fabrics, paper, cellulose, and mixtures thereof.

The fabric which is employed in the sheet-like substrate may comprise from 20% to 80% by weight of polypropylene, and from 20% to 80% by weight of viscous rayon.

When there is a plurality of sheet-like substrates which are arranged in the dispensing enclosure for dispensing therefrom one sheet at a time, the individual sheet-like substrates may be configured so as to be rolled in sheets which are separable at perforations between adjacent sheets, or in interleaved sheets, stacked sheets, or stacked folded sheets.

Typically, the dispensing enclosure which is employed in keeping with the present invention may be a sealable canister which has a cruciform dispensing opening formed at one end thereof, a sealable box which has a reclosable lid at the top thereof, resealable pouches having a dispensing slit on one side surface thereof, or resealable pouches having a resealable opening at one end thereof.

Typically, the sheets of the substrate are rectangular, and may have edge dimensions ranging from 7.5 cm by 7.5 cm up to 25 cm by 25 cm.

The amount of self-tanning composition which is infused into the sheet-like substrate in keeping with the present invention, is infused in an amount which is in the range of 0.015 grams per cm$^2$ up to 0.022 grams per cm$^2$.

The present invention also provides a method for infusing a plurality of sheet-like substrates with an aqueous self-tanning composition. The sheet-like substrates and the aqueous self-tanning composition is as described above.

The method of infusing a plurality of sheet-like substrates with the aqueous self-tanning composition comprises the following steps:

(a) A plurality of sheet-like substrates is placed into a sealable vacuum chamber. The sealable vacuum chamber is such that it has agitation means in the interior thereof which causes agitated movement of the plurality of sheet-like substrates when placed therein. Also, the sealable vacuum chamber is capable of being rotated about an axis so as to cause a tumbling movement of the plurality of sheet-like substrates when they are placed therein. The sealable vacuum chamber is equipped with an injection port.

(b) The vacuum chamber is sealed.

(c) The interior of the vacuum chamber is heated to a temperature of 105° C. to 115° C. and is maintained at that temperature for a period of 30 to 35 minutes. During that period of time, the sheet-like substrates in the vacuum chamber are tumbled and agitated.

(d) Then, the interior of the vacuum chamber is cooled to a temperature of 70° C. to 75° C., where the cooling is carried out at a rate of 5° C. per 15 minutes.

(e) A vacuum is then drawn in the interior of the vacuum chamber, to a gauge vacuum in the range of 27 cm Hg to 42 cm Hg.

(f) Then, an aqueous extract of Japanese green tea is introduced into the vacuum chamber, while maintaining the temperature of step (d). Thereafter, the plurality of sheet-like substrates is tumbled and agitated for a period of 20 to 25 minutes.

(g) The interior of the vacuum chamber is then cooled to 62° C. to 67° C., at a rate of 5° C. per 15 minutes.

(h) The humectant is then introduced into the vacuum chamber while maintaining the temperature of step (g), and the plurality of sheet-like substrates is tumbled and agitated for a period of 12 to 18 minutes.

(i) The interior of the vacuum chamber is cooled once again to 48° C. to 52° C., at a rate of 5° C. per 15 minutes.

(j) Then, minerals are introduced into the vacuum chamber while maintaining the temperature at that of step (i), and again the sheet-like substrates are tumbled and agitated for a period of 28 to 38 minutes.

(k) A further cooling step is carried out, cooling the interior of the vacuum chamber to a temperature of 43° C. to 47° C., also at a rate of 5° C. per 15 minutes.

(l) The ethoxydiglycol and PPG-12-Buteth-16 are premixed, and then the dihydroxyacetone is added to the premix so as to form an homogenous mixture.

(m) Then the homogenous mixture is introduced into the vacuum chamber, while maintaining the temperature of step (k). Once again, the plurality of sheet-like substrates is tumbled and agitated for a period of 38 to 48 minutes.

(n) The interior of the vacuum chamber is again cooled to a temperature of 28° C. to 32° C., again at a rate of 5° C. per 15 minutes.

(o) Thereafter, the vacuum in the vacuum chamber is relieved and the vacuum chamber is opened. The plurality of infused sheet-like substrates are then removed from the vacuum chamber for packaging in groups of pluralities thereof into dispensing enclosures therefor.

Typically, the sealable vacuum chamber has a double-walled structure, and step (c) is carried out by injecting steam into the chamber formed by and between the two walls of the double-walled structure.

The formulation is as described above, and may include a number of alternative and additional additives as noted above.

If those additives are to be employed, then a further step (p) is carried out as follows:

(p) After step (m), the interior of the vacuum chamber is cooled to a temperature of 35° C. to 39° C., at a rate of 5° C. per 15 minutes.

Thereafter, after step (p) is carried out but before step (n) is carried out, any one or more of the following steps may be employed:

(q) The bacillus ferment is introduced into the vacuum chamber while maintaining the temperature of step (p), and the plurality of sheet-like substrates is tumbled and agitated for a period of 12 to 18 minutes.

(r) The frankincense extract is introduced into the vacuum chamber while maintaining the temperature of step (p), and the plurality of sheet-like substrates is tumbled and agitated for a period of 12 to 18 minutes.

(s) The skin protectant is introduced into the vacuum chamber while maintaining the temperature of step (p), and the plurality of sheet-like substrates is tumbled and agitated for a period of 12 to 18 minutes.

(t) The cosmetically acceptable and compatible colorant is introduced into the vacuum chamber while maintaining the temperature of step (p), and the plurality of sheet-like substrates is tumbled and agitated for a period of 12 to 18 minutes.

(u) The antioxidant is introduced into the vacuum chamber while maintaining the temperature of step (p), and the plurality of sheet-like substrates is tumbled and agitated for a period of 12 to 18 minutes.

(v) EDTA is introduced into the vacuum chamber while maintaining the temperature of step (p), and the plurality of sheet-like substrates is tumbled and agitated for a period of 12 to 18 minutes.

(w) The tanning accelerator is introduced into the vacuum chamber while maintaining the temperature of step (p), and the plurality of sheet-like substrates is tumbled and agitated for a period of 12 to 18 minutes.

(x) The cosmetically acceptable and compatible preservative is introduced into the vacuum chamber while maintaining the temperature of step (p), and the plurality of sheet-like substrates is tumbled and agitated for a period of 12 to 18 minutes.

(y) The stabilizer is introduced into the vacuum chamber while maintaining the temperature of step (p), and the plurality of sheet-like substrates is tumbled and agitated for a period of 12 to 18 minutes.

(z) The natural essential oils are introduced into the vacuum chamber while maintaining the temperature of step (p), and the plurality of sheet-like substrates is tumbled and agitated for a period of 12 to 18 minutes.

Any of the above steps (q) through (z) may be employed, but those steps which are employed are typically carried out in the order in which they are described above.

When the tanning composition further comprises from 0.5% to 20% by weight of the sunscreen, then the sunscreen is introduced into the vacuum chamber following step (q)—or in any event following step (p) when step (q) is not employed—and the plurality of sheet-like substrates is tumbled and agitated for a period of from 28 minutes to 38 minutes.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

Figure 1:
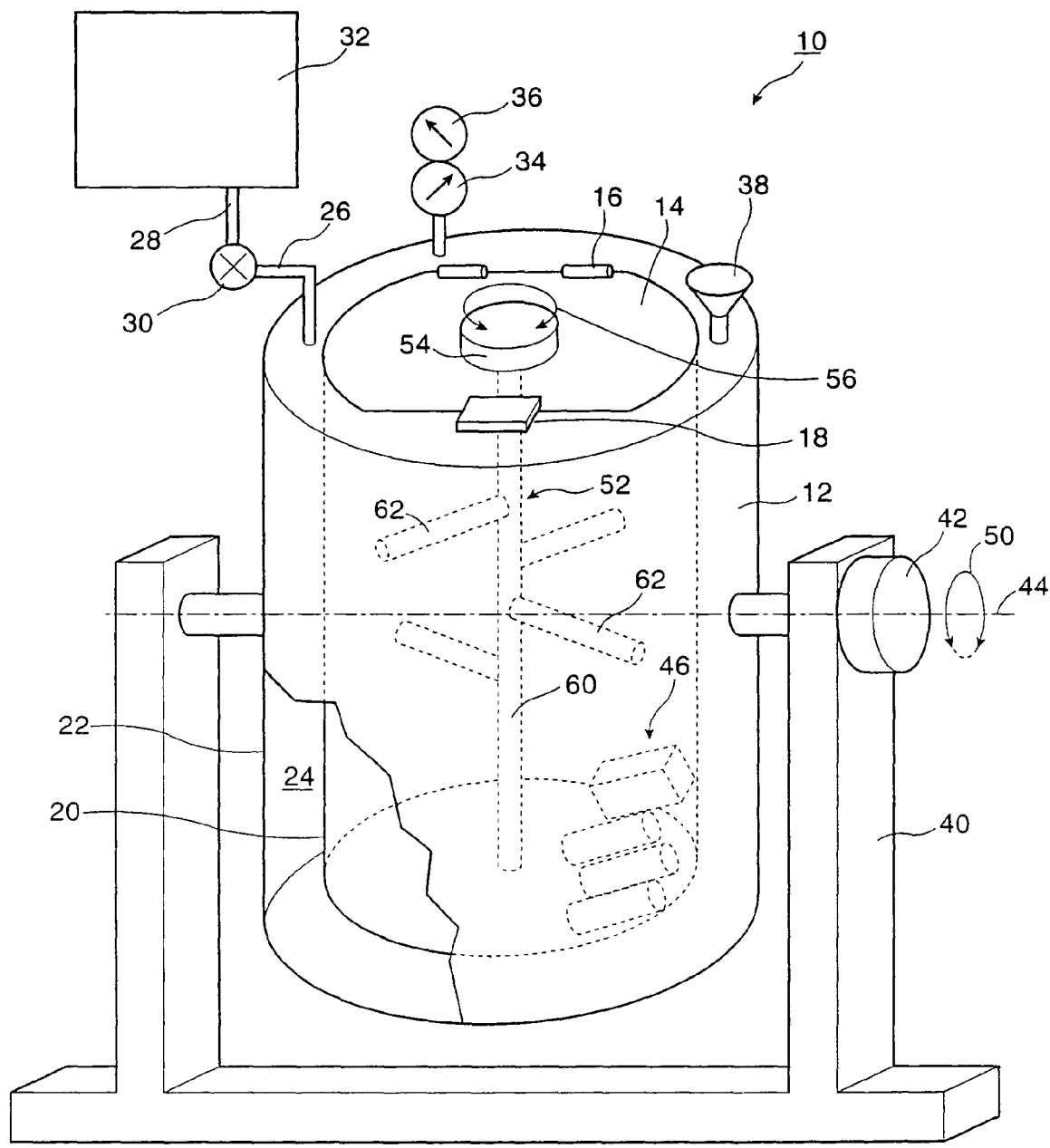
FIG. 1 is a diagrammatic view of a typical vacuum chamber of the sort employed to carry out the methods of the present invention.

The novel features which are believed to be characteristic of the present invention, as to its structure, organization, use and method of operation, together with further objectives and advantages thereof, will be better understood from the following discussion.

As noted above, the present invention provides a plurality of sheet-like substrates in a dispensing enclosure, where the sheet-like substrates are each infused with a self-tanning composition.

Essentially, the nature of the sheet-like substrate is well known, comprising woven fabrics, non-woven fabrics, paper, cellulose, and mixtures thereof. These sheet-like substrates are commonly used in towelettes and wipes of various kinds, such as those which may be available in hermetically sealed packages that are distributed in restaurants and the like for cleansing one's hands after a meal. Other typical uses for such sheet-like substrates are in wipes that are used particularly during the care of an infant—such as when the diaper of the infant is being changed—as well as in many medical and surgical situations where an antiseptic is to be wiped onto the surface of the skin.

A typical fabric composition which is employed in sheet-like substrates such as those used in the present invention will comprise from 20% up to 80% by weight of polypropylene, and from 20% up to 80% by weight of viscous rayon. Such polypropylene/viscous rayon fabrics are resistant to tearing, but have a physical structure whether woven or non-woven such that they may be infused with a liquid such as the aqueous self-tanning composition of the present invention.

The present invention contemplates that at least two—generally, a plurality in the order of 15, 30, or 50—sheet-like substrates which are infused with the self-tanning composition will be sold in a single dispensing enclosure as a self-tanning composition application dispensing set. Typically, the self-tanning composition is applied to parts of the body which are desired to have the "tanned look"; and typically such application may be to a major portion of the skin of the user—if not all of the body.

Moreover, in order to achieve the desired tanned appearance, it is typical that application of a self-tanning composition to the skin will occur over a number of days, with a deeper looking tanned appearance occurring after several sequential applications of the self-tanning composition. Accordingly, it is appropriate to supply to the user a plurality of sheet-like substrates in a single dispensing enclosure.

Since the sheet-like substrates of the present invention have been infused with the aqueous self-tanning composition of the present invention, they are damp to the touch; but the present invention provides a method whereby the self-tanning composition will not migrate away from the sheet-like substrate until such time as it is applied to the skin so as to transfer from the sheet-like substrate onto the skin of the user. This fact also permits the provision of a plurality of sheet-like substrates in a dispensing enclosure, but the dispensing enclosure is generally such that it can be sealed so as to preclude evaporation.

The nature of the container is also one which is well known from the cleansing wipe industry. Essentially, similar or identical containers can be used, and they typically are in the form of a circular or oval cylinder, a rectilinear box, or a pocket pouch. Typically, if a cylindrical dispensing enclosure is employed, it is sealable by having a hinged closure which covers a cruciform dispensing opening through which the sheet-like substrate or towelette extends for dispensing one at a time. Those sheet-like substrates are dispensed from a roll, from the inside to the outside of the roll, and are typically separated by perforations between each towelette on the roll. In other forms, such as a sealable box having a reclosable lid, the sheet-like substrates are typically placed in the manner of interleaved sheets or stacked sheets. Other dispensing enclosures include pouches which may have a dispensing slit on one side surface thereof, or a resealable opening at one end thereof, through which the sheet-like substrates are again dispensed one at a time. Typically, the sheet-like substrates are folded and stacked when placed into a pouch.

The size of the sheet-like substrate may vary, although typically the shape is such as to be rectangular. A common size is 12.7 cm by 20.3 cm (5 inches by 8 inches), although other sizes may be employed. The sheet-like substrates may be as small as 7.5 cm by 7.5 cm (approximately 3 inches by 3 inches), and they may be as large as 25 cm by 25 cm (approximately 10 inches by 10 inches).

The self-tanning composition is an aqueous composition, and its principal ingredients include the following:
- 45% to 65% by weight of aqueous extract of Japanese green tea
- 5% to 15% by weight of dihydroxyacetone
- 5% to 25% by weight of ethoxydiglycol
- 3% to 10% by weight of PPG-12-Buteth-16
- 1% to 13% by weight of a humectant
- 0.05% to 0.5% by weight of cosmetically acceptable and compatible minerals Further optional ingredients that may be used, in any combination thereof, include the following:
- 0.5% to 5% by weight of bacillus ferment
- 0.5% to 5% by weight of frankincense extract
- 0.1% to 7.5% by weight of a skin protectant
- 0.1% to 6% by weight of a cosmetically and acceptable and compatible colorant
- 0.5% to 1.5% by weight of tocopherol
- 0.1% to 1% by weight of disodium ethylenediamine tetraacetic acid (EDTA)
- 1% to 5% by weight of a tanning accelerator
- 0.5% to 1% by weight of a cosmetically acceptable and compatible preservative
- 0.5% to 1% by weight of PPG-40-castor oil
- 0.1% to 0.5% by weight of natural essential oils The purpose of each of the ingredients which is used, either as a required ingredient or optionally, is now described:

Aqueous extract of Japanese green tea is a compound which contains ferric ferrous salt, and a salt of an alkali metal. Indeed, ferric salt is added to an aqueous solution of a strong acid, and then a salt of an alkali metal or compound containing a metal is added. A typical mixture may be a stable mixture of ferric ferrous chloride, which is known to have great absorption abilities. The absorption abilities are also enhanced by the polyphenolic compounds of Japanese green tea. The stable mixture controls ionization, and is also a mineral enhanced and fortified substance that contains catechins. The aqueous extract of Japanese green tea increases the activity of the other ingredients which are found in the self-tanning composition formulation.

Dihydroxyacetone is, of course, the compound which promotes the self-tanning or tanning effect when applied to the skin. Application of dihydroxyacetone to the skin promotes migration of melanin—the naturally occurring dark pigment in the skin—to the surface of the skin.

Ethoxydiglycol functions as an emollient. It also has the ability to carry the active ingredient of the composition, and helps those active ingredients to penetrate into the skin faster.

PPG-12-Buteth-16 also functions as an emollient, it helps to carry the active ingredients of the composition, and helps to penetrate into the skin faster.

The humectant may be butylene glycol in an amount of 1% to 5% by weight, or it may be 1% to 8% by weight of glycerine, or mixtures thereof. Butylene glycol exhibits an anti-microbial action. It also functions as a humectant that is resistant to high humidity. Glycerine—which is a by-product of soap manufacture—is a sweet and warm tasting oily fluid which is obtained by adding alkalis to fats and fixed oils. It also functions as a humectant, and is used often in moisturizers due to its water-binding capabilities which allow it to draw and absorb water from the air. Glycerine helps to retain skin moisture, and is employed because it is non-toxic, non-irritating, and non-allergenic.

The cosmetically acceptable and compatible minerals may be one or more of the following: C.I. #15985, #77492, #77491, #77499, #77718, #42090, #16035. The minerals serve two purposes. First, they function as part of a colorant which may be employed to enhance a ruddy or tanned glow appearance of the skin. Their other important function is to generate electrolytes during the infusion process, so as to assure infusion and capture of the various other ingredients in the matrix of the sheet-like substrate.

More particular details concerning the cosmetically acceptable and compatible minerals are as follows, with reference to their Color Index (C.I.) Numbers:
- C.I. # 15985 is FD&C Yellow No. 6
- C.I. # 77492 is Iron Oxide Orange
- C.I. # 77491 is Iron Oxide Orange
- C.I. # 77499 is Iron Oxide Black
- C.I. # 77718 is Iron Oxide Yellow
- C.I. # 42090 is FD&C Blue No.1, Aluminum Lake
- C.I. # 16035 is FD&C Red No. 40, Aluminum Lake.

Bacillus ferment is an active exfoliant ingredient having an enzymatic nature. The bacillus ferment enzyme is a protease which is selected for its activity and stability, and is obtained by fermentation of the micro-organism *Bacillus Subtillis*. Liposomes are catezomes that have the ability to encapsulate the bacillus ferment within a natural structure which is biologically compatible to the skin.

The frankincense extract, when employed, serves the purpose of a moisturizer. It is also an anti-inflammatory agent and a mild antiseptic which brings relief to dry and sensitive skin types and helps to heal wounds. Its astringent properties are said to help balance oily or overactive skin. The use of frankincense extract, an essential oil, is said to date back to ancient Egypt.

The skin protectant which is employed may comprise 0.5% to 2.5% by weight of aloe vera gel, from 0.5% to 4% by weight of hydrocotyl extract, from 0.1% 5 to 1% by weight of myrrh extract, and mixtures thereof. Aloe vera gel is the mucilage which is obtained from aloe vera leaves, and it is a well known botanical which is used for healing, anti-microbial hydrating, softening, and moisturizing of the skin.

Hydrocotyl extract is traditionally used for couperose condition. It is also used for soothing and anti-itching treatments in dermatological disorders.

Myrrh extract is said to have disinfectant, antiseptic, anti-inflammatory, anti-itching, cicatrizant, tonic, stimulant, sedative, and astringent properties. It also functions as a good fixative. Myrrh extract is valuable in products which are designed for all skin types. Myrrh is a traditional and ancient ingredient that has been used in perfumes and incense, and was used by ancient Egyptian women in facial masks and other cosmetic preparations.

The cosmetically acceptable and compatible colorant which may be employed includes not only the minerals discussed above, but may also comprise from 1% to 5% by weight of walnut extract from 0.1% to 1% by weight of caramel, and mixtures thereof, together with the minerals. Walnut extract is traditionally used topically for soothing and anti-itching, as well against sunburns and other superficial burns. It has fungistatic and astringent properties, and is used in cases of acne and skin diseases. The oil is extracted from the ripe nut, although extracts may also be obtained from the leaves and bark. Walnut extract functions as a natural colorant for tanning purposes.

Caramel is also used as a coloring agent and provides products having a slight brownish color. Caramel is also said to act as a soothing agent in some skin care preparations.

Tocopherol is employed as an anti-oxidant. Tocopherol is known, in one form, as Vitamin E, and may be any one of the group of closely related, fat-soluble alcohols which behave similar to Vitamin E, and are present in milk, lettuce, wheat germ oil, and some other vegetable oils. Tocopherol also functions as a photoprotectant and it is an oil-soluble anti-oxidant and free radical scavenger. Tocopherol also functions as a preservative, due to its ability to protect against oxidation; and as a moisturizer it is well absorbed through the skin, demonstrating a strong affinity with small blood vessels. Tocopherol is used in topical applications prior to exposure to ultraviolet radiation, and protects against epidermal cell damage in such circumstances.

EDTA functions as a preservative and an anti-oxidant. It is a commonly used substance in cosmetics, and is used primarily as a sequestering agent.

The tanning accelerator which is employed may be chosen from the group consisting of acetyl-L-tyrosine, hydrolyzed vegetable protein, adenosine triphosphate, riboflavin, and mixtures thereof.

Acetyl-L-tyrosine is a natural plant complex which grants and accelerates a more intense tanned appearance. The same function is also achieved by any other of the tanning accelerators noted immediately above.

The cosmetically acceptable and compatible preservative which may be employed in formulations according to the present invention are chosen from the group which consists of methyl paraben, dimethylol dimethyl (DMDM) hydantoin, and iodopropynyl butylcarbamate, and mixtures thereof. Methyl paraben is a water phase preservative because it has a very low sensitizing potential. It is well known as a preservative which is used to combat bacteria and moulds. It therefore provides bacteriostatic and fungistatic activity against a number of various organisms, and is safe for use in cosmetics.

DMDM hydantoin is also a popular preservative that has a moderate sensitizing potential. It is one of the fastest growing cosmetic preservatives, used worldwide, and has an excellent safety record when used in leave-on and wash-off cosmetic preparations. Iodopropynyl butylcarbamate is also a preservative that has broad fungicidal and anti-bacterial activity, and is recommended for use in sensitive skin formulations.

PPG-40-castor oil functions as a stabilizer, and is a solublizer for natural essential oils.

Various natural essential oils of the sort known in the cosmetics industry may be employed.

The present invention also contemplates the further addition of a sunscreen in the amount of from 0.5% to 20% by weight, in the self-tanning composition. The sunscreen may, itself, be chosen from the group which consists of from 1% to 20% by weight of methoxycinnamate, from 1% to 20% by weight of octyl salicylate, from 1% to 10% by weight of benzophenone-3, from 0.5% to 10% by weight of benzophenone-4, and mixtures thereof.

Turning now to FIG. 1, which shows the principal features of an apparatus which is used to infuse a plurality of sheet-like substrates with an aqueous self-tanning composition in keeping with the present invention, the following discussion is directed to the process by which the plurality of sheet-like substances is infused with the aqueous self-tanning composition.

The apparatus 10 comprises a sealable vacuum chamber 12 having a sealable hatch or cover 14. The structure of the vacuum chamber 12 is outside the scope of the present invention. Typically, the cover 14 may be hinged at 16, with a latch 18 being provided to ensure that the cover or hatch 14 remains in a sealed and locked position, when necessary.

Typically, the vacuum chamber is a double-walled structure, having an interior wall 20 and an exterior wall 22. In essence, the vacuum chamber 12 comprises a cylinder having wall 20 being placed inside a cylinder having wall 22, with a chamber 24 being formed between the walls 20 and 22.

Steam may be injected into the chamber 24 through pipes 26 and 28, under control of valve 30, from a source of steam 32.

The interior of the vacuum chamber 12 may be evacuated by a vacuum pump, not shown, and suitable gauges 34, 36 are employed to indicate the level of vacuum and the temperature of the interior of the vacuum chamber 12, respectively.

Various ingredients may be introduced into the vacuum chamber through such as a funnel 38 or any other convenient injection port, as is well known.

The vacuum chamber 12 is conveniently mounted on such as a stand 40, which is provided with an appropriate motor or other drive means 42 to rotate the vacuum chamber 12 about an axis 44. This provides a tumbling action, whereby a plurality of rolls or stacks of sheet-like substrates 46, shown in the interior of the vacuum chamber 12, has a tumbling movement imparted thereto. The tumbling motion of the vacuum chamber 12 may be continuously in one or the other direction about the axis 44, or alternately in one direction and then in the other direction, all as indicated at double arrow 50.

Within the interior of the vacuum chamber 12 there is an agitator structure 52—typically, a centrally disposed vertical rod 60 having a plurality of arms 62 extending perpendicularly therefrom and disposed radially at varying angles around the rod 60. An appropriate motor means or other drive means 54 is provided to impart an agitation or oscillatory movement to the agitator structure 52, first in one direction and then the other about its axis, as indicated by double arrow 56.

The operation of the apparatus 10 is fairly simple: a plurality of stacks or rolls of sheet-like substrates, as shown at 46, is placed in the interior of the vacuum chamber 12, and various steps which are described below are carried out after the vacuum chamber 12 is closed and sealed by closing the cover 14. Various constituents of the self-tanning composition—all of which are flowable in one form or another—are inserted such as through the injection port 38. The interior volume of the vacuum chamber 12 may be heated by introducing steam into the chamber 24, and cooling of the interior of the vacuum chamber 12 is effected by releasing steam and/or by introduction of suitable cooling gases or liquids, into the chamber 24. Such arrangements are outside the scope of the present invention, and are such that they are dictated by the precise structure of the vacuum chamber 12.

The first step is to place a plurality of rolls or piles 46 of sheet-like substrates into the interior of the vacuum chamber 12, which comprises step (a) described as follows:

(a) Placing a plurality of sheet-like substrates in a sealable vacuum chamber 12, wherein the sealable vacuum chamber has agitation means 52 in the interior thereof to cause agitated movement of the plurality of sheet-like substrates 46 when placed therein, wherein the sealable vacuum chamber is capable of being rotated about an axis 44 so as to cause a tumbling movement of the plurality 46 of sheet-like substrates which are placed in the interior of the vacuum chamber 12, and wherein the sealable vacuum chamber 12 has an injection port 38.

This is followed by step (b), sealing the vacuum chamber.

Step (c) then requires that the interior of the vacuum chamber be heated to a temperature of 105° C. to 115° C., and maintained at that temperature for a period of 30 to 35 minutes. During that period of time, the plurality 46 of sheet-like substrates in the interior of the vacuum chamber 12 is tumbled and agitated as shown by double arrows 50 and 56.

At this time, the plurality 46 of sheet-like substrates has been sterilized, and the sheet-like substrates have been conditioned to allow them to be infused with the ingredients of the self-tanning composition, as described hereafter.

Step (d) then follows: the interior of the vacuum chamber is cooled to a temperature of 70° C. to 75° C. at a rate of 5° C. per 15 minutes.

This is followed by step (e), which draws a vacuum into the interior of the vacuum chamber to a gauge vacuum which is in the range of 27 cm Hg to 42 cm Hg.

After the vacuum has been drawn in step (e), step (f) comprises the introduction of the aqueous extract of Japanese green tea into the vacuum chamber while maintaining the temperature which was established during step (d). The plurality 46 of sheet-like substrates in the interior of the vacuum chamber is tumbled and agitated, this time for a period of 20 to 25 minutes.

Step (g) then follows, wherein the interior of the vacuum chamber 12 is cooled once again, to a temperature in the range of 62° C. to 67° C., at a rate of 5° C. per 15 minutes.

Step (h) then follows. The humectant—butylene glycol, glycerine, and mixtures thereof, in the quantities discussed above—is then introduced into the vacuum chamber 12. The plurality 46 of sheet-like substrates is then tumbled and agitated at the temperature established in step (g) for a period of 12 to 18 minutes.

Step (i) then follows, in which the interior of the vacuum chamber is cooled once again to a temperature of 48° C. to 52° C. at a rate of 5° per 15 minutes.

Then, step (j) comprises the introduction of minerals into the vacuum chamber while maintaining the temperature which was established in step (i); and once again tumbling and agitating the plurality 40 of sheet-like substrates for a period of 28 to 38 minutes.

Step (k) then follows, in which the interior of the vacuum chamber is cooled once again: this time to a temperature of 43° C. to 47° C., at a rate of 5° C. per 15 minutes.

This is followed by step (1), in which the ethoxydiglycol and PPG-12-Buteth-16 are premixed, and then the dihydroxyacetone is added to the premix so as to form an homogeneous mixture.

Then, in step (m), the homogenous mixture is introduced into the vacuum chamber while, once again, maintaining the temperature of the interior of the vacuum chamber at the temperature established in step (k). The plurality 46 of sheet-like substrates is tumbled and agitated for a period of 38 to 48 minutes.

In step (n), which follows, the interior of the vacuum chamber is cooled to a temperature of 28° C. to 32° C., once again at a rate of 5° C. per 15 minutes.

Thereafter, in step (o), the vacuum in the vacuum chamber is relieved, the vacuum chamber is opened, and the plurality of infused sheet-like substrates is removed from the interior of the vacuum chamber 12 for packaging in groups of pluralities thereof into the appropriate dispensing enclosures therefore. Typically, the infused sheet-like substrates which have become wipes or towelettes infused with the self-tanning composition, are handled by forceps or other appropriate material handling apparatus. It will be recalled that the temperature of the plurality 46 of sheet-like substrates is still in the range of 28° C. to 32° C., at least for a while after the vacuum chamber 12 has been opened.

As noted above, there may be a number of other constituents that are optionally included in the formulation of the self-tanning composition which is to be infused into the plurality 46 of sheet-like substrates. If so, those additional constituents are added following step (m)—where the homogenous mixture of ethoxydiglycol. PPG-12-Buteth-16, and dihydroxyacetone—is introduced into the vacuum chamber whose temperature is in the range of 43° C. to 47° C. and before the interior of the vacuum chamber is cooled to a temperature of 28° C. to 32° C. as required in step (n).

Accordingly, following step (m), step (p) is carried out, in which the interior of the vacuum chamber is cooled to a temperature of 35° C. to 39° C., at a rate of 5° C. per 15 minutes.

Thereafter, following step (p) but before step (n), any or all of the following steps may be carried out. Typically, when any of the following steps are carried out, they are performed in the order in which they are discussed below. Each of the steps which are discussed below takes place with the interior temperature in the vacuum chamber being held at a temperature of 35° C. to 39° C., as established in step (p); and each of the steps which follows includes the action of tumbling and agitating the plurality 46 of sheet-like substrates for a period of 12 minutes to 18 minutes.

Step (q) involves introduction of the bacillus ferment into the vacuum chamber.

Step (r) involves introduction of the frankincense extract into the vacuum chamber.

In step (s), the skin protectant is introduced into the vacuum chamber.

Step (t) involves introducing the cosmetically acceptable and compatible colorant into the vacuum chamber.

Step (u) involves introduction of the anti-oxidant into the vacuum chamber.

In step (v), EDTA is introduced into the vacuum chamber.

Step (w) calls for introduction of the tanning accelerator, into the vacuum chamber.

Step (x) involves introduction of the cosmetically acceptable and compatible preservative into the vacuum chamber.

Step (y) involves introduction of the stabilizer into the vacuum chamber.

Step (z) involves introducing the natural essential oils into the vacuum chamber.

As noted, in each instance, each of the above steps is carried out at the temperature established in step (p), and involves tumbling and agitating the plurality 46 of sheet-like substrates for a period of 12 to 18 minutes.

When a sunscreen is employed, which sunscreen is as described above, then the sunscreen is introduced into the vacuum chamber after step (q)—when the bacillus ferment is introduced into the vacuum chamber—and in this case the plurality 46 of sheet-like substrates are tumbled and agitated for a period of from 28 minutes to 38 minutes.

The quantity of each of the ingredients which are used, that is put into the vacuum chamber 12 during the various steps described above, is such that the amount of the self-tanning composition which infuses into each sheet-like substrate is, in the aggregate, in the range of 0.0115 g/cm$^2$ to 0.022 g/cm$^2$. For example, with a load of 4500 to 5000 sheets of 12.7 cm by 20.3 cm size, from 20 to 25 total kilograms of the ingredients of th self-tanning formulation are infused into sheet-like substrates.

The present invention has provided a set of sheeted self-tanning composition infused sheet-like substrates, which are provided in a dispensing enclosure therefore, from which the infused sheet-like substrates are dispensed one sheet at a time.

The specific self-tanning composition, including ranges of constituents thereof, and including optional additional constituents, has been described and explained.

A method has been taught by which the plurality of sheet-like substrates is infused with the self-tanning composition. Once the sheet-like substrates have been infused with the self-tanning composition, the self-tanning composition is stable within the matrix of the sheet-like substrate until it is transferred to the skin by having the sheet-like substrate—the wipe or towelette—applied to the surface of the skin.

The present invention has also provided a method for manufacturing the plurality of sheet-like substrates having the self-tanning composition infused therein. The method is fairly time consuming, but results in an extremely stable product so that unwanted unattractive streaking and blotching of the skin will not occur as the self-tanning composition is applied to the skin.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

What is claimed is:

1. A sheeted self-tanning composition application dispensing set comprising of a plurality of sheeted substrates and a dispensing enclosure;
    wherein each of said sheeted substrates is infused with an aqueous self-tanning composition; and
    wherein said plurality of sheeted substrates is arranged in said dispensing enclosure for dispensing therefrom one sheet at a time;
    wherein each said sheeted substrate is such that said aqueous self-tanning composition adheres thereto when said sheeted substrate is within said dispensing enclosure, and is such that said aqueous self-tanning composition will transfer therefrom when said sheeted substrate is applied to the skin of a user;
    and wherein said aqueous self-tanning composition comprises from 45% to 65% by weight of aqueous extract of Japanese green tea, from 5% to 25% by weight of dihydroxyacetone, from 5% to 25% by weight of ethoxydiglycol, from 3% to 10% by weight of PPG-12-Buteth-16 as an emollient, from 1% to 13% by weight of a humectants, and from 0.05% to 0.5%, by weight of cosmetically acceptable and compatible minerals.

2. The sheeted self-tanning composition application dispensing set of claim 1, wherein said self-tanning composition further comprises further cosmetically acceptable and compatible additives chosen from the group consisting of from 0.5% to 5% by weight of bacillus ferment as an enzyme exfoliator, from 0.5% to 5% by weight of frankincense extract as a moisturizer, from 0.1% to 7.5% by weight of a skin protectant, from 0.1% to 6% by weight of a cosmetically acceptable and compatible colorant, from 0.5% to 1.5% by weight of tocopherol as an anti-oxidant, from 0.1% to 1% by weight of disodium ethylenediamine tetraacidic acid (EDTA), from 1% to 5% by weight of a tanning accelerator, from 0.5% to 1% by weight of a cosmetically acceptable and compatible preservative, from 0.5% to 1% by weight of PPG-40-castor oil as a stabilizer, from 0.1% to 0.5% by weight of natural essential oils, and mixtures thereof.

3. The sheeted self-tanning composition application dispensing set of claim 2, wherein said humectant is chosen from the group consisting of 1% to 5% by weight of butylene glycol, from 1% to 8% by weight of glycerine, and mixtures thereof;
    wherein said skin protectant is chosen from the group consisting of 0.5% 5 to 2.5% by weight of aloe vera gel, from 0.5% to 4% by weight of hydrocotyl extract, from 0.1% to 1% by weight of myrrh extract, and mixtures thereof;
    wherein said cosmetically acceptable and compatible colorant is chosen from the group consisting of 1% to 5% by weight of walnut extract, 0.1% to 1% by weight of caramel, and mixtures thereof, together with said minerals;
    wherein said minerals are chosen from the group consisting of C.I. #15985, #77492, #77491, #77499, #77718, #42090, #16035, and mixtures thereof;
    wherein said tanning accelerator is chosen from the group consisting of acetyl-L-tyrosine, hydrolyzed vegetable protein, adenosine triphosphate, riboflavin, and mixtures thereof;
    and wherein said cosmetically acceptable and compatible preservative is chosen from the group consisting of methyl paraben, dimethylol dimethyl hydantoin, and iodopropynyl butylcarbamate, and mixtures thereof.

4. The sheeted self-tanning composition application dispensing set of claim 1, wherein said self-tanning composition further comprises from 0.5% to 20% by weight of sunscreen chosen from the group consisting of from 1% to 20% by weight of octyl methoxycinnamate, from 1% to 20% by weight of octyl salicylate, from 1% to 10% by weight of benzophenone-3, from 0.5% to 10% by weight of benzophenone-4, and mixtures thereof.

5. The sheeted self-tanning composition application dispensing set of claim 1, wherein the material of said plurality of sheeted substrates is chosen from the group consisting of woven fabrics, non-woven fabrics, paper, cellulose, and mixtures thereof.

6. The sheeted self-tanning composition application dispensing set of claim 5, wherein said fabrics have a composition which comprises from 20% to 80% by weight of polypropylene, and from 20% to 80% by weight of viscose rayon.

7. The sheeted self-tanning composition application dispensing set of claim 1, wherein said plurality of sheeted substrates is arranged in a manner chosen from the group consisting of a plurality of sheeted substrates rolled in sheets which are separable at perforations therebetween, interleaved sheets, stacked sheets, and stacked folded sheets.

8. The sheeted self-tanning composition application dispensing set of claim 7, wherein said dispensing enclosure is chosen from the group consisting of sealable canisters having a cruciform dispensing opening formed at one end thereof, sealable boxes having a reclosable lid at the top thereof, resealable pouches having a dispensing slit on one side surface thereof, and resealable pouches having a resealable opening at one end thereof.

9. The sheeted self-tanning composition application dispensing set of claim 1, wherein each one of said plurality of sheeted substrates is rectangular, and has a size in the range of 7.5 cm by 7.5 cm up to 25 cm by 25 cm.

10. The sheeted self-tanning composition application dispensing set of claim 9, wherein each one of said plurality of sheeted substrates is infused with an amount of said aqueous self-tanning composition in the range of 0.015 g/cm$^2$ to 0.022 g/cm$^2$.

11. A method of infusing a plurality of sheeted substrates with an aqueous self-tanning composition;
wherein each of said plurality of sheeted substrates has a surface area in the range of from 55 cm$^2$ to 625 cm$^2$;
wherein the material of said plurality of sheeted substrates is chosen from the group consisting of woven fabrics, non-woven fabrics, paper, cellulose, and mixtures thereof;
wherein each one of said plurality of sheeted substrates is infused with an amount of said aqueous self-tanning composition in the range of 0.015 g/cm$^2$ to 0.022 g/cm$^2$;
and wherein said aqueous self-tanning composition comprises from 45% to 65% by weight of aqueous extract of Japanese green tea, from 5% to 15% by weight of dihydroxyacetone, from 5% to 25% by weight of ethoxydiglycol, from 3% to 10% by weight of PPG-12-Buteth-16 as an emollient, from 1% to 13% by weight of a humectant, and from 0.05% to 0.5% by weight of cosmetically acceptable and compatible minerals;
wherein said method comprises the steps of: (a) placing a plurality of sheeted substrates in a sealable vacuum chamber, wherein said sealable vacuum chamber has agitation means in the interior thereof to cause agitated movement of said plurality of sheeted substrates when placed therein, wherein said sealable vacuum chamber is capable of being rotated about an axis so as to cause a tumbling movement of said plurality of sheeted substrates when placed therein, and wherein said sealable vacuum chamber has an injection port;
(b) sealing said vacuum chamber;
(c) heating the interior of said vacuum chamber to a temperature of 105° C. to 115° C., and maintaining that temperature for a period of from 30 to 35 minutes, while tumbling and agitating said plurality of sheeted substrates;

(d) cooling said interior of said vacuum chamber to a temperature of 70° C. to 75° C., at a rate of 5° C. per 15 minutes;
(e) drawing a vacuum in the interior of said vacuum chamber to a gauge vacuum in the range of 27 cm Hg to 42 cm Hg;
(f) introducing said aqueous extract of Japanese green tea into said vacuum chamber while maintaining said temperature of step (d), and tumbling and agitating said plurality of sheeted substrates for a period of 20 to 25 minutes;
(g) cooling said interior of said vacuum chamber to a temperature in the range of 62° C. to 67° C., at a rate of 5° C. per 15 minutes;
(h) introducing said humectant into said vacuum chamber while maintaining said temperature of step (g), and tumbling and agitating said plurality of sheeted substrates for a period of 12 to 18 minutes;
(i) cooling said interior of said vacuum chamber to a temperature of 48° C. to 52° C., at a rate of 5° C. per 15 minutes;
j) introducing said minerals into said vacuum chamber while maintaining said temperature of step (i), and tumbling and agitating said plurality of sheeted substrates for a period of 28 to 38 minutes;
(k) cooling said interior of said vacuum chamber to a temperature of 43° C. to 47° C., at a rate of 5° C. per 15 minutes;
(l) premixing said ethoxydiglycol and said PPG-12-Buteth-16, and adding said dihydroxyacetone thereto, to form a homogenous mixture;
(m) introducing said homogenous mixture into said vacuum chamber while maintaining said temperature of step (k), and tumbling and agitating said plurality of sheeted substrates for a period of 38 to 48 minutes;
(n) cooling said interior of said vacuum chamber to a temperature of 28° C. to 32° C., at a rate of 5° C. per 15 minutes;
(o) relieving said vacuum, opening said vacuum chamber, and removing said plurality of infused sheeted substrates therefrom for packaging in groups of pluralities thereof into dispensing enclosures therefor.

12. The method of claim 11, wherein said sealable vacuum chamber has a double-walled structure, and step (c) is carried out by injecting steam into the chamber formed by and between the two walls of said double-walled structure.

13. The method of claim 11, wherein said self-tanning composition further comprises further cosmetically acceptable and compatible additives chosen from the group consisting of from 0.5% to 5% by weight of bacillus ferment as an enzyme exfoliator, from 0.5% to 5% by weight of frankincense extract as a moisturizer, from 0.1% to 7.5% by weight of a. skin protectant, from 0.1% to 6% by weight of a cosmetically acceptable and compatible colorant, from 0.5% to 1.5% by weight of tocopherol as an anti-oxidant, from 0.1% to 1% by weight of disodium ethylenediamine tetraacidic acid (EDTA), from 1% to 5% by weight of a tanning accelerator, from 0.5% to 1% by weight of a cosmetically acceptable and compatible preservative, from 0.5% to 1% by weight of PPG-40-castor oil as a stabilizer, from 0.1% to 0.5% by weight of natural essential oils, and mixtures thereof.

14. The method of claim 12, wherein said humectant is chosen from the group consisting of 1% to 5% by weight of butylene glycol, from 1% to 8% by weight of glycerin, and mixtures thereof;

wherein said skin protectant is chosen from the group consisting of 0.5% to 2.5% by weight of aloe vera gel, from 0.5% to 4% by weight of hydrocotyl extract, from 0.1% to 1% by weight of myrrh extract, and mixtures thereof;

wherein said cosmetically acceptable and compatible colorant is chosen from the group consisting of 1% to 5% by weight of walnut extract, 0.1% to 1% by weight of caramel, and mixtures thereof, together with said minerals;

wherein said minerals are chosen from the group consisting of C.I. #15985, #77492, #77491, #77499, #77718, #42090, #16035, and mixtures thereof;

wherein said tanning accelerator is chosen from the group consisting of acetyl-L-tyrosine, hydrolyzed vegetable protein, adenosine triphosphate, riboflavin, and mixtures thereof;

and wherein said cosmetically acceptable and compatible preservative is chosen from the group consisting of methyl paraben, dimethylol dimethyl hydantoin, and iodopropynyl butylcarbarnate, and mixtures thereof.

15. The method of claim 13, further comprising the step of:
(p) after step (m), cooling said interior of said vacuum chamber to a temperature of 35° C. to 39° C. at a rate of 5° C. per 15 minutes;
and wherein said method further comprises further steps carried out after step (p) and before step (n);
wherein said further steps are chosen from the group consisting of the following steps, and mixtures thereof:
(q) introducing said bacillus ferment into said vacuum chamber while maintaining said temperature of step (p), and tumbling and agitating said plurality of sheeted substrates for a period of 12 to 18 minutes;
(r) introducing said frankincense extract into said vacuum chamber while maintaining said temperature of step (p), and tumbling and agitating said plurality of sheeted substrates for a period of 12 to 18 minutes;
(s) introducing said skin protectant into said vacuum chamber while maintaining said temperature of step (p), and tumbling and agitating said plurality of sheeted substrates for a period of 12 to 18 minutes;
(t) introducing said cosmetically acceptable and compatible colorant into said vacuum chamber while maintaining said temperature of step (p), and tumbling and agitating said plurality of sheeted substrates for a period of 12 to 18 minutes;
(u) introducing said anti-oxidant into said vacuum chamber while maintaining said temperature of step (p), and tumbling and agitating said plurality of sheeted substrates for a period of 12 to 18 minutes; (v) introducing said EDTA into said vacuum chamber while maintaining said temperature of step (p), and tumbling and agitating said plurality of sheeted substrates for a period of 12 to 18 minutes;
(w) introducing said tanning accelerator into said vacuum chamber while maintaining said temperature of step (p), and tumbling and agitating said plurality of sheeted substrates for a period of 12 to 18 minutes;
(x) introducing said cosmetically acceptable and compatible preservative into said vacuum chamber while maintaining said temperature of step (p), and tumbling and agitating said plurality of sheeted substrates for a period of 12 to 18 minutes;
(y) introducing said stabilizer into said vacuum chamber while maintaining said temperature of step (p), and tumbling and agitating said plurality of sheeted substrates tbr a period of 12 to 18 minutes; and
(z) introducing said natural essential oils into said vacuum chamber while maintaining said temperature of step (p), and tumbling and agitating said plurality of sheeted substrates for a period of 12 to 18 minutes.

16. The method of claim 15, wherein said self-tanning composition further comprises from 0.5% to 20% by weight of sunscreen chosen from the group consisting of from 1% to 20% by weight of octyl methoxycinnamate, from 1% to 20% by weight of octyl salicylate, from 1% to 10% by weight of benzophenone-3, from 0.5% to 10% by weight of benzophenone-4, and mixtures thereof;
wherein said sunscreen is introduced into said vacuum chamber following step (q); and
wherein said plurality of sheeted substrates are tumbled and agitated for a period of from 28 to 38 minutes.

17. A sheeted substrate infused with an aqueous self-tanning composition such that said aqueous self-tanning composition adheres thereto will transfer therefrom when said sheeted substrate is applied to the skin of a user, wherein:
said aqueous self-tanning composition comprises from 45 to 65 by weight of aqueous extract of Japanese green tea, from 5% to 15% by weight of dihydroxyacetone, from 5% to 25% by weight of ethoxydiglycol, from 3% to 10% by weight of PPG-12-Buteth-16 as an emollient, from 1% to 13%by weight of a humectant, and from 0.05% to 0.5%, by weight of cosmetically acceptable and compatible minerals.
the material of said sheeted substrates is chosen from the group consisting of woven fabrics, non-woven fabrics, paper, cellulose, and mixtures thereof; and
each one of said plurality of sheeted substrates is infused with an amount of said aqueous self-tanning composition in the range of 0.015 g/cm$^2$ to 0.022 g/cm$^2$.

* * * * *